US008642057B2

(12) United States Patent
Code et al.

(10) Patent No.: US 8,642,057 B2
(45) Date of Patent: Feb. 4, 2014

(54) ANTIMICROBIAL AND ANTIODOR SOLUTIONS AND DELIVERY SYSTEMS

(75) Inventors: Kenneth R. Code, Edmonton (CA); Joseph L. Provenzano, Huntington Beach, CA (US); Richard D. Bickerstaff, Phoenix, AZ (US)

(73) Assignee: Biolargo Life Technologies, Inc., La Mirada, CA (US)

( * ) Notice: Subject to any disclaimer, the term of this patent is extended or adjusted under 35 U.S.C. 154(b) by 91 days.

(21) Appl. No.: 13/308,105

(22) Filed: Nov. 30, 2011

(65) Prior Publication Data

US 2012/0087965 A1     Apr. 12, 2012

Related U.S. Application Data

(63) Continuation-in-part of application No. 12/009,586, filed on Jan. 18, 2008, now Pat. No. 8,226,964.

(60) Provisional application No. 61/490,448, filed on May 26, 2011.

(51) Int. Cl.
*A01N 25/02*     (2006.01)

(52) U.S. Cl.
USPC ......... 424/405; 424/76.8; 424/76.9; 424/406; 424/667; 424/668; 424/669; 424/670; 424/671; 424/637; 424/638

(58) Field of Classification Search
USPC ......... 424/408, 417–420, 455, 490–495, 637, 424/638, 667–671; 514/608, 962, 963
See application file for complete search history.

(56) References Cited

U.S. PATENT DOCUMENTS

| 3,516,941 | A | 6/1970 | Matson |
| 3,860,565 | A | 1/1975 | Barber, Jr. |
| 4,056,610 | A | 11/1977 | Barber, Jr. et al. |
| 4,756,906 | A | 7/1988 | Sweeny |
| 5,433,953 | A | 7/1995 | Tsuei et al. |
| 5,589,194 | A | 12/1996 | Tsuei et al. |
| 5,804,298 | A | 9/1998 | Moy |
| 6,413,548 | B1 | 7/2002 | Hamer et al. |
| 7,867,510 | B2 * | 1/2011 | Code ............................ 424/443 |
| 8,257,749 | B2 * | 9/2012 | Code ............................ 424/667 |
| 2003/0194447 | A1 * | 10/2003 | Scholz et al. ................. 424/672 |
| 2011/0124504 | A1 * | 5/2011 | Oester et al. ................. 504/206 |

* cited by examiner

*Primary Examiner* — Neil Levy
(74) *Attorney, Agent, or Firm* — Mark A. Litman & Associates, P.A.

(57) ABSTRACT

Antimicrobial solutions and delivery systems for them use liquid antimicrobial solutions with:
  at least 80% of total weight of a carrier liquid comprising water, alcohol or a mixture of water and alcohol;
  at least 0.0001% by weight of the solution of $I^2$;
  at least 0.0001% by weight of $CuSO_4$; and
  sufficient acid in the solution top provide a pH of less than 7.0.

A buffering system is also preferable in the solution, and the solution may be provided directly as a liquid, as a spray, as a gel, imbibed and carried in a wipe, encapsulated solution, segregated droplets of solution (in carrying layers of particles, dispersed in a solid of gel carrier) and the like.

6 Claims, No Drawings

ANTIMICROBIAL AND ANTIODOR SOLUTIONS AND DELIVERY SYSTEMS

RELATED APPLICATIONS DATA

This application claims priority as a continuation-in-part application under 35 U.S.C. 120 from U.S. patent application Ser. No. 12/009,586, filed Jan. 18, 2008 and Provisional U.S. Patent Application Ser. No. 61/490,448, filed May 26, 2011.

BACKGROUND OF THE INVENTION

1. Field of the Invention

The present invention relates to the field of antimicrobial solutions, anti-odor solutions and delivery systems for the solutions.

2. Background of the Art

Iodine solutions have been used for over a century as a disinfectant. Further advances in the performance and stability of iodine solutions are desirable.

SUMMARY OF THE INVENTION

A liquid antimicrobial solution is provided which may contain by way of non-limiting examples:
1. A liquid antimicrobial solution comprising:
    at least 80% of total weight of a carrier liquid comprising water, alcohol or a mixture of water and alcohol;
    at least 0.001% by weight of the solution of I2; and
    sufficient acid in the solution to provide a pH of less than 6.5.

Another description is a solution as:
    at least 80% of total weight of a carrier liquid comprising water, alcohol or a mixture of water and alcohol;
    at least 0.0005% by weight of the solution of I2 (e.g., at least 10, at least 15 or at least 20 ppm) and/or I⁻; and
    sufficient acid in the solution to provide a pH of less than 6.5.

An alternative solution may contain, by way of non-limiting examples:
    0.001% by weight (or at least 10 ppm of the solution) of the solution of a cation (e.g., K⁺) and a solution of I₂ (and some residual I⁻);
    at least 0.001% by weight of CuSO₄; and
    sufficient acid in the solution to provide a pH of less than 6.5.

These solutions of the present invention may be provided in numerous formats.

DETAILED DESCRIPTION OF THE INVENTION

One aspect of technology described herein includes a liquid antimicrobial solution with:
A) at least 80% of total weight of a carrier liquid comprising water, alcohol or a mixture of water and alcohol;
    at least 0.0005% by weight of the solution of I₂; (e.g., 0.0005 to 0.10% by weight, 10-100 ppm, 10-80 ppm, 10-50 ppm, 10-30 ppm iodine), and/or I⁻ and
    sufficient acid (even with buffering) in the solution to provide a pH of less than 7.0, preferably less than 6.5; or
B) at least 80% of total weight of a carrier liquid comprising water and dissolved iodine, alcohol or a mixture of water and alcohol;
    at least 0.001% by weight of the solution of (I2 (e.g., 0.0005 to 0.10% by weight, 10-100 ppm, 10-80 ppm, 10-50 ppm, 10-30 ppm iodine), and/or I⁻;) and cation (e.g., K⁺) and residual, non-critical, equilibrium I⁻;

at least 0.001% by weight of of the solution of CuSO₄; and sufficient acid in the solution top provide a pH of less than 5.0.

The solution may have acid in sufficient amount to provide an initial pH of from 2.0 to 4.8 or 3.5 to 6.0, and then be buffered to moderate the pH to a less acidic (but still acidic) level. The solution has a preferred acid of sulfamic acid and may then be buffered back to a pH of 5.8-7.0, preferably 6.0-6.5.

The solutions of the present technology may be provided, by way of non-limiting examples, wherein the acid is sufficient in an amount to provide a pH of from 5.5 to 6.7, especially where the acid comprises a sulfamic acid compound, such as a sulfamic acid compound having the formula:

wherein R is independently selected from the group consisting of hydrogen and electron-withdrawing groups, or a sulfamic acid compound having the formula:

wherein R is independently selected from the group consisting of hydrogen, halogen, cyano, C1-C6 alkyl, C1 to C6 substituted alkyl, perhalo alkyl, halosubstituted alkyl, and electron-withdrawing groups.

One embodiment may have least one R as hydrogen, or exactly one R as hydrogen. A spherical encapsulation system may be provided as a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. For example, the encapsulation system may have the core as a droplet of the solution having a diameter of from 0.0001 to 1 mm. The encapsulation system may have the droplet of solution comprises 10-90% average percentage by weight of the encapsulation system.

Another encapsulation system comprising droplet cores of aqueous liquids comprising the solution of the present technology having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections. The layer of hydrophobic particles may be a layer of particles with less than 80% by number of said particles being bonded to any adjacent particle.

One additional subgeneric format includes a microencapsulated particles comprising a frangible shell having a liquid core of the solution of the present technology. The frangible shell may be a polymer and the microencapsulated particles have a number average diameter of 0.001 to 2 mm (or larger, such as up to 5 mm).

Another additional subgeneric format includes an iodine delivery system comprising a hydrocolloid entraining at least 20 by weight of the delivery system of the solution of the present technology.

Still another iodine delivery system includes a clay entraining at least 20 by weight of the delivery system of the solution of the present technology or an iodine delivery system comprising a flexible polymer having droplets of the solution of the technology disclosed herein dispersed therein. This last iodine delivery system may have the droplets with a number average diameter of 0.001 to 2 mm.

The present solution technology may be delivered in a variety of different formats, depending upon the specific use and needs of individual environments and technical applications. The material may be directly applied as a liquid, or brought in a protected mode (e.g., so the liquid solution does not immediately flow (e.g., encapsulated, gelled, imbibed, entrained, etc.). The following descriptions are examples of specific embodiments within the scope of the generic invention.

1. Gel with Iodine and Boron to Control Radiation Leaks

This aspect of the technology prescribes that the chemical basis of nuclear fuel control rods (boron from boric acid, hafnium, cadmium) be suspended in our CupriDyne-SAP™ gel to a desired consistency without breaking the gel, and then disposing on spent fuel rods, fuel rods, and other nuclear plant containment vessels and areas, to absorb neutrons, and cool down the target. This is useful when water cannot be used, but desirable also in that the flocculent of SAP will acquire the fission products as well, and prevent exposure to alpha, beta, and most gamma rays. Just as firefighting using fire retardant chemicals is dropped from the air, likewise a gel will adhere to all surfaces to cool down the spill or problem rods. In essence, it is a gelled version of a control rod which can be pumped by emergency pumpers. Water with boric acid has been tried by the Japanese, but the amount of boric acid is limited to 3-5%, especially in sea water—not enough to cool down the fuel rods, and then the water leaked out from containment in the particular instance, anyway.

Other organic and inorganic polymers and thixotropic agents may be used to increase the viscosity of the solutions or even gel the solutions. Silicas, acrylics, clays, natural resins and oils and waxes, viscofiers and other known additives may be used alone or in combination with stabilizing or emulsifying agents to form solutions, thick solutions, gels of other flowable compositions. Additional polymers and additives such as cellulosic materials (e.g., carboxy alkyl celluloses, such as carboxy methyl cellulose), polyalkylene glycols, phthalates, alcohols, dyes, indicators and the like can be used in the solutions.

2. Stable Iodine Liquid Compositions/Solutions (Ready to Use and Concentrate)

An iodine solution is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive antimicrobial effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters (e.g., 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The inventor has noted that the addition of sulfamic acid (in particular) to all CupriDyne198 treatment composition formulas can provide ultimate stability or even enhanced activity in its various antimicrobial or surface treatment procedures. The sulfamic acid is both an acidifying agent (and other acids may be used) and a primitive surfactant. CupriDyne™ antimicrobial compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula. The solutions may have normal levels of iodine therein (e.g., at least 5 ppm or may be concentrated for dilution with greater than 50 ppm, greater than 100 ppm, greater than 200 ppm, up to solubility limits of iodine in aqueous or alcohol solvents.

The solution is preferred where the acid comprises a sulfamic acid compound having the formula:

$NR_2SO_3H$, wherein R is independently selected from the group consisting of hydrogen and electron-withdrawing groups. The acid may comprise a sulfamic acid compound having the formula:

$NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

The solution may have at least one R is hydrogen in the sulfamic acid compound or only and exactly one R is hydrogen.

These solutions are antimicrobial, have anti-odor effects, and can bleach or remove some stains.

The solutions have been found to be even further improved by buffering to keep the pH of the solution within an optimum range of between 5.8-7.5, more preferably between 5.8 and 6.5, and still more preferably between 6.0 and 6.4. Preferred buffering agents include inorganic cation buffering agents such as carbonates, bicarbonates, phosphates and other inorganic basic salts. Sodium, calcium, potassium and lithium salts of the buffering agents are preferred, but ammonium salts may also be used. The buffering of the solution surprisingly adds significant value to the solutions including at least one of storage stability, aerial stability, reduced cell toxicity, reduced corrosiveness, reduced corrosive action on dentures and bone and the like.

It has also been found that the order of mixing certain combinations of ingredients simplifies the dissolution of individual ingredients and improves some final solutions properties (such as transparency). For example, it has been found that first dissolving the buffering agent or the acid, and then dissolving the acid or buffering agent, respectively, makes it easier to dissolve the active components and make it easier to provide a transparent active iodine solution. The two iodine-forming reactive ingredients may then be added into the acid-buffer solution. The $CuSO_4$ may be first dissolved into the acid-buffer solution and then the alkali or alkaline iodide is dissolved in the acid-buffer/$CuSO_4$ solution. The iodide may be added as Li, Na, K, Ca, Mg, $NH_4$ iodide or the like. In certain medical and environmental uses, the selection of the particular cation may be more than merely a matter of convenience or choice of equivalents. The particular cation may be desirable as Na in certain medical applications where Li or K is less desirable. The various cations may be selected for design and concentration to maintain an appropriate isotonic balance with patients and their cells and vessels. The concentration of the cations and anions and iodine in solution, the pH and the selection of particular incidental cations and anions are selected to achieve balances of properties in the solutions.

The solutions of the present technology may be added to, combined with and/or modified to replicate other known medical solutions, as with the case of "Normal" saline, where 0.9% w/w NaCl in sterile water is involved, so that it s possible to compute the Na content to include a change from KI to NaI in this technology. This can be used to create a solution with 260 to 310 mOsm/L osmolality, or preferablye between 275 and 300 mOsm/L osmolality, and approach balance with the normal Na or cation pressure in tissue. In one preferred embodiment, sodium iodide replaces portions of (5%, 10%, 20%, 30%, 50%, 60%, 75%, 80%, 90%, 95%) or all of the potassium iodide.

On another level, a lactated Ringer's solution is possible. "One litre of lactated Ringer's solution ordinarily contains:

130 mEq (80-200) of sodium ion=130 mmol/L
109 mEq (70-180) of chloride ion=109 mmol/L
28 mEq (15-50) of lactate=28 mmol/L
4 mEq (2-8) of potassium ion=4 mmol/L
3 mEq (1.5-4) of calcium ion=1.5 mmol/L"

An equivalent or partial replacement equivalent or mixture with solutions according to the present technology may also be prepared. The sodium, chloride, potassium, calcium and chloride in the standard lactated Ringer's solution may vary among each other by percentages n the order of (5%, 10%, 20%, 30%, 50%, 60%, 75%, 80%, 90%, and 95%) among each other.

These stable solutions are advantageously deliverable in many different forms, besides direct liquid delivery as a wipe, spray or brush application. For example, the solutions may be provided as a spherical encapsulation system comprising a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. The core may, for example, comprise a droplet of the solution having a diameter of from 0.0001 to 1 mm. The encapsulation system may have the droplet of solution comprises 10-90% average percentage by weight of the encapsulation system. These solutions may be directly applied, sprayed, imbibed in a fabric carrier and applied as a wipe, or gelled and the like.

3. Encapsulated or Microencapsulated Delivery Systems

Another format is as an encapsulation system comprising droplet cores of aqueous liquids comprising the solution of the present technology having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections. The layer of hydrophobic particles may comprise a layer of particles with less than 80% by number of said particles being bonded to any adjacent particle. This technology is enabled in U.S. Pat. No. 6,413,548. By this technology, generally non-compatible materials may be provided from a single delivery system by a unique encapsulation system. An encapsulation system is advantageously constructed as a core of aqueous liquid having at least 5% by weight water therein, and an encapsulant surrounding the core to form a stable encapsulated particle, the encapsulant comprising at least one layer of hydrophobic particles in contact with and surrounding the core, the core and hydrophobic particles providing an encapsulated system that has an average weight average particle diameter of from 0.05 to 25 micrometers and can support its own weight. The encapsulation system may be provided by a novel method of manufacture comprising providing a mass of hydrophobic particles having average mass diameter size of between 0.05 and 25 micrometers, providing droplets of an aqueous medium to the mass of particles, gently mixing the fine particles of aqueous medium and the hydrophobic particles to form a stable encapsulant system of droplets of the aqueous medium encapsulated by a shell of particles.

Another format of liquid solution delivery is as a microencapsulated particles comprising a frangible shell having a liquid core of the solution of the present technology. The microencapsulated particles may have a frangible shell that comprises a polymer and the microencapsulated particles have a number average diameter of 0.001 to 2 mm. Such technology for forming the shells with liquid fill is enabled as microcapsules produced through interfacial polymerization having shell walls composed of polyamides, polyureas, polyurethanes, and polyesters are known; see U.S. Pat. Nos. 3,516,941, 3,860,565, 4,056,610, and 4,756,906. Alternative enabling methods include U.S. Pat. Nos. 5,433,953, 5,589,194. and 5,804,298.

4. Entrained Solution Delivery Systems

Another iodine delivery system may be as a hydrocolloid entraining at least 20 by weight of the delivery system of the solution of the present technology or as an iodine delivery system comprising a clay entraining at least 20 by weight of the delivery system of the solution of the present technology.

5. Aqueous Solution Entrapped in Polymeric Medium

Another alternative liquid delivery system may be as an iodine delivery system comprising a flexible polymer having droplets of the solution of the present technology dispersed therein. This form of liquid delivery system, may for example, use droplets have a number average diameter of 0.001 to 2 mm.

Droplets of aqueous solution may be suspended, dispersed or emulsified within a hardenable (driable or polymerizable) film forming polymeric composition. The hardenable film-forming polymer (which is inclusive of elastomers) is then hardened by dryiving off solvents (drying) or polymerizing the solution or neat (little or no solvent) polymerizable composition to stably entrain the droplets of solution within the hardened film. Rather than droplets, frangible microcapsules or water-beads as disclosed in U.S. Pat. No. 6,413,548 (cite above) may be blended into the hardenable polymeric composition, which is then hardened.

The liquids and stabilized (e.g., encapsulated) liquid solutions of the present technology may be used in a wide variety of environments. The liquid solutions may be applied directly to surfaces such as surgical tables, surgical tool trays, surgical tools, surgical tubing; dental tools; equestrian wares such as bits, spurs, metal harness loops, silverware, kitchen sinks and cooking tools; animal sheds, animal coup walls and floors and the like. The encapsulated or stabilized solutions may be added to a wide range of products to add antimrobial or antiodor properties to otherwise conventional products such as papers, napkins, placemats, animal bedding, animal litter, bandages, wraps, sanitary napkins, wound dressings, bed covers, bed pads, transportation wrappings for food (e.g., wrapping paper for fruit, and tray covers for meat), and the like. The solutions and their delivery systems may be included in sealing waxes, seals (e.g., elastomeric tubing and joint seals and washers), animal chew toys (e.g., using the droplet distribution in the elastomer/polymer, or adding a coating layer of polymer with droplets or encapsulated solutions to provide releasable iodine solution from a surface subject to abrasion or pressure).

Frangible encapsulants of the presently described technology, when entrained in insulation media such as styrofoam or fiber batts, add phase change temperature control around the freezing point of the liquid fill. Phase-change insulation media, once frozen and packaged for infectious samples (for example) will delay a package warmup when exposed to ambient temperatures to assist with sample or specimen preservation. In the event that warmup ultimately occurs, the pre-frozen capsules which have expanded at the freezing point of aqueous fill will deploy their contents into the insulation media. The presently described iodine solutions in this format are therefore a broad spectrum oxidative countermeasure against the contents of the samples or specimens which have likely leaked their contents as well.

Similarly, the liquid solutions of the present technology, when frozen, may be provided to contain clathrates of stabilized free iodine which are active oxidizers in solution upon progressive melting. This is a countermeasure against fouling during refrigerated transportation of foods, and at ambient retail outlets with the foods on display.

One skilled in the arts related to this technology, including antiseptic and antimicrobial fields, polymer chemistry, emulsion chemistry and encapsulation technology can provide specific alternatives and equivalents within the scope of the generic disclosure and enablement disclosed herein.

Each reference cited in this disclosure are incorporated by reference in their entirety.

What is claimed:

1. A liquid antimicrobial solution comprising: at least 80% of total weight of a carrier liquid comprising water, alcohol or a mixture of water and alcohol; at least 0.001% by weight of the solution of $I_2$; and sufficient acid in the solution to provide a pH of less than 6.5, and the solution further comprising IK and at least 0.005% by weight of $CuSO_4$, a sulfamic acid compound and a buffering agent.

2. The solution of claim 1 wherein the acid comprises a sulfamic acid compound having the formula: $NR_2SO_3H$, wherein R is independently selected from the group consisting of hydrogen and electron-withdrawing groups.

3. The solution of claim 1 wherein the acid comprises a sulfamic acid compound having the formula: $NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

4. The solution of claim 3 wherein at least one R is hydrogen.

5. The solution of claim 1 wherein the buffering agent comprises a carbonate, bicarbonate or phosphate.

6. The solution of claim 3 wherein the buffering agent comprises a carbonate, bicarbonate or phosphate.

* * * * *